United States Patent [19]

Watson

[11] Patent Number: Plant 6,040

[45] Date of Patent: Oct. 20, 1987

[54] AMELANCHIER SHRUB NAMED "PRINCE WILLIAM"

[76] Inventor: Thomas Watson, 1746 Highway 73, Cambridge, Wis. 53523

[21] Appl. No.: 705,616

[22] Filed: Feb. 26, 1985

[51] Int. Cl.[4] ..... A01H 5/00

[52] U.S. Cl. ..... Plt./51

[58] Field of Search ..... Plt./51

[56] References Cited

U.S. PATENT DOCUMENTS

P.P. 3,092 4/1972 Flemer ..... Plt. 51

OTHER PUBLICATIONS

Weaver, Richard E., Jr., "The Shadbushes", *Arnoldia,* vol. 34, No. 1, (1974) pp. 21–31.

DeWolf, Gordon, "Shadbush", *Horticulture,* vol. 60, No. 5, (1982), p. 22.

Fernald, M. L. *Gray's Manual of Botany,* (8th ed) American Book Company (1950) p. 766 only.

Rehder, Alfred, *Manual of Cultivated Trees and Shrubs,* (2nd ed) The Macmillan Company (1960), p. 388 only.

*Primary Examiner*—James R. Feyrer

*Attorney, Agent, or Firm*—Isaksen, Lathrop, Esch, Hart & Clark

[57] ABSTRACT

A new variety of *Amelanchier canadensis* is disclosed which is characterized by its large flowers, averaging 2 centimeters in size, which give rise to full form, densely packed, large, sweet fruit, up to ½ inch in size which are thus large, plentiful, and easily harvested.

3 Drawing Figures

1

The present invention relates to a new and distinct variety of *Amelanchier canadensis* which was found in a cultivated area.

The distinct characteristics of the suckering shrub of the present invention are that new shoot sprouts arise from the ground at a close proximity to the base of the shrub, giving the plant a unique, full form, that the shrub produces densely-packed large, sweet fruit easily picked and that the shrub's thick glossy leaves withstand hot and humid summers that defoliate other Amelanchier shrubs.

The variety is derived from a plant which is believed to be, as confirmed by solicited expert opinion, as most properly classified as *Amelanchier canadensis.* Some experts, however, believe it may be a hybrid derived from an *A. canadensis* parent and an unknown Amelanchier parent because of the large blossom size and the densely pubescent ovary.

Asexual reproduction of the new variety was accomplished by tissue culture of new bud cells, and showed that the foregoing characteristics and distinctions come true to form and are established and transmitted through succeeding propagations.

The accompanying drawing shows a typical shrub specimen of the new variety, together with typical flower and fruit specimens on a larger scale.

The following is a detailed description of the new variety, with color terminology in accordance with the Inter-Society Color Council—National Bureau of Standards Circular 553 Color Chart, except where general color terms of ordinary dictionary significance are obvious.

Parentage: Bud cells.

*Seed parents.*—Unnamed specimens of *Amelanchier canadensis* and an unknown Amelanchier.

Propagation: Holds its distinguishing characteristics through succeeding propagations by tissue culture.

Locality where discovered: a cultivated yard in Madison, Wis.

2

Locality where propagated and grown: Cambridge, Wis.

Shrub: Grows to an average of 8–10 feet tall.

Trunk: Slender; smooth.

*Color.*—Gray-Brown, Hue No. 62; Fall color, red to orange.

Branches: Thick, smooth.

*Color.*—Reddish Brown, Hue No. 43.

Foliage:

*Leaves.*—Thick, waxy.

*Quantity.*—Abundant.

*Length.*—Average 7 cm.

*Width.*—Average 5 cm.

*Shape.*—Oval-lanceolate.

*Color.*—Upper surface very dark yellow green, Hue No. 138; under surface — dark yellow green, Hue No. 137.

*Margin.*—Serrate; serrations about 1 mm deep and average 0.3 cm apart.

*Petiole and veins.*—Reddish, Hue No. 13, length of petiole 1.3 cm.

Flower Buds:

*Hardiness.*——30F.

*Size.*—Length average 0.9 cm. Width average 0.5 cm.

*Shape.*—Globular.

*Color.*—Yellow white; Hue No. 92.

Flowers:

*Quantity.*—Abundant April 15, Zone 4.

*Size.*—Average 2 cm in diameter.

*Petalage.*—5 petals. Shape — rounded. Size: Length, average 1 cm; Width, average 0.7 cm. Color: White; Hue No. 263.

Fruits: Sweet.

*Borne.*—Average June 20, Zone 4.

*Abundance.*—Abundant.

*Shape.*—Globular.

*Size.*—Length average 1.0 cm. Width average 1.2 cm.

*Color.*—Very deep red purple; Hue No. 243.

Winter buds: Fat and slightly blunted.

I claim:

1. A new and distinct variety of *Amelanchier canadensis,* substantially as herein shown and described, characterized particularly as to novelty by its large flowers averaging 2 centimeters in diameter, its unique, full form, densely packed large, sweet fruit, up to ½" in size, easily picked, and thick glossy leaves which can withstand hot and humid summers without defoliating.

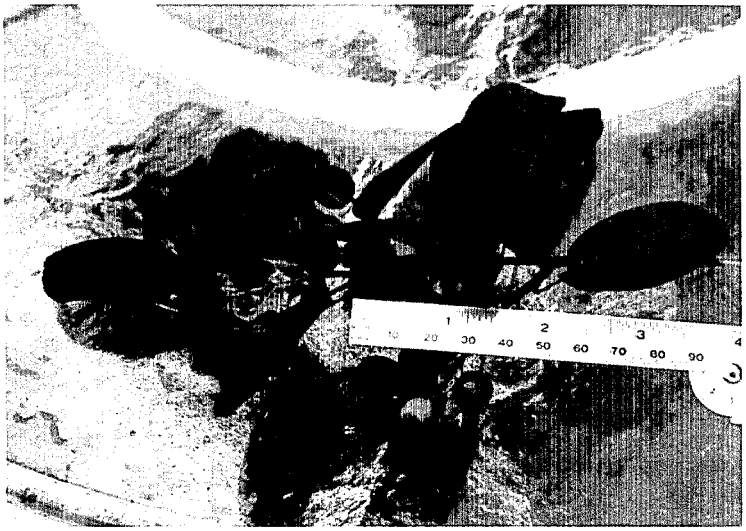
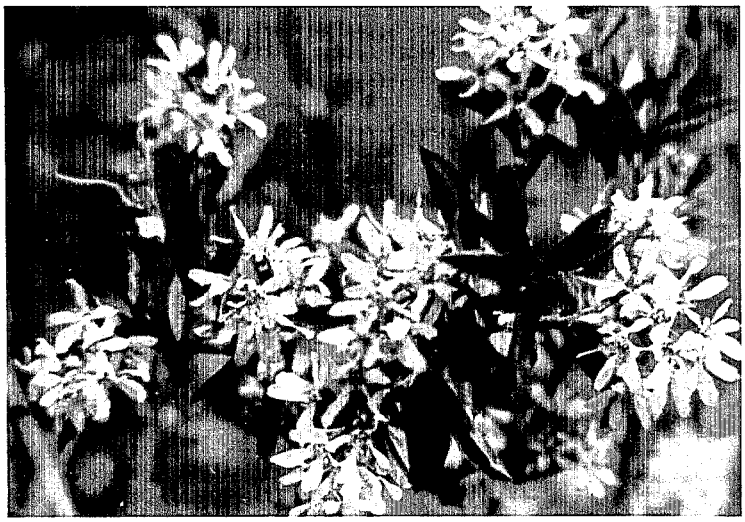
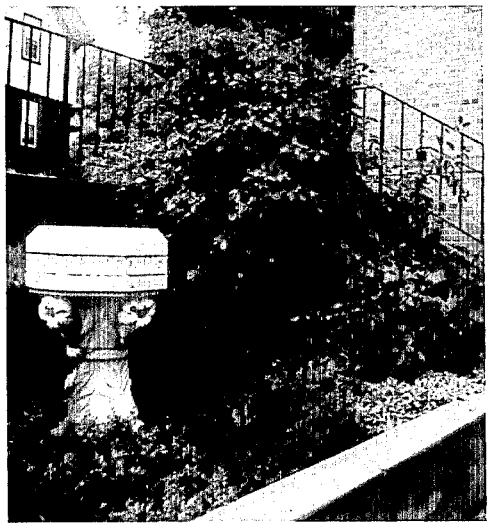

* * * * *